(12) United States Patent
Karlen et al.

(10) Patent No.: US 9,909,999 B2
(45) Date of Patent: Mar. 6, 2018

(54) SYSTEMS AND METHODS FOR RADIOGRAPHIC INSPECTION

(71) Applicant: Delavan Inc, West Des Moines, IA (US)

(72) Inventors: Eric Karlen, Rockford, IL (US); William L. Wentland, Rockford, IL (US)

(73) Assignee: Delavan Inc., West Des Moines, IA (US)

( * ) Notice: Subject to any disclaimer, the term of this patent is extended or adjusted under 35 U.S.C. 154(b) by 311 days.

(21) Appl. No.: 14/671,006

(22) Filed: Mar. 27, 2015

(65) Prior Publication Data

US 2016/0282285 A1 Sep. 29, 2016

(51) Int. Cl.
*G01N 23/04* (2006.01)
*G01N 23/18* (2018.01)

(52) U.S. Cl.
CPC .......... *G01N 23/046* (2013.01); *G01N 23/18* (2013.01); *G01N 2223/404* (2013.01); *G01N 2223/409* (2013.01)

(58) Field of Classification Search
CPC .......... G01N 2223/409; G01N 23/046; G01N 23/18; G01N 2223/645; G01N 23/2273; G01N 15/088; B23Q 17/20; B23Q 17/24; C09K 3/1009; F16J 15/102; G21K 1/06; G21K 2201/064; H01J 37/256; G05B 19/401; A61B 17/1703; A61B 17/1725; A61B 17/3403; A61B 2017/00902; A61B 90/39; G01V 5/0008; B01L 2200/0678; B01L 2300/0829; B01L 2300/0858; B01L 2300/0893; B01L 3/5085; B25J 17/0266; B25J 9/0072; B25J 9/106; B25J 9/1065; B29C 37/0082; B29C 39/10; B29C 39/123
(Continued)

(56) References Cited

U.S. PATENT DOCUMENTS 6,182,437 B1 * 2/2001 Prociw .................... F23D 11/36
60/776
6,183,497 B1 2/2001 Sing et al.
(Continued)

FOREIGN PATENT DOCUMENTS

WO  WO 2014081940 A1 *  5/2014  ............. A61B 19/54
WO  WO-2014081940 A1   5/2014

OTHER PUBLICATIONS

Michaeli, W., Schrickte, L., & Berdel, K. (Apr. 2009). Structural Analysis of Polymeric foam. In Proceedings of the Skyscan User Meeting 2009 (pp. 51-54).*
(Continued)

*Primary Examiner* — Irakli Kiknadze
(74) *Attorney, Agent, or Firm* — Locke Lord LLP; Scott D. Wofsy; Christopher J. Cillié

(57) ABSTRACT

An inspection method include introducing a mixture of expanding foam and a particulate material into a region of interest of an object, fixing the powder within the region of the interest relative to the object, and acquiring image data of the object and particulate mixture using an x-ray source and an x-ray detector. The particulate has a density that is greater than the density of a material forming the object to provide contrast between the region of interest and the object in an image generated using the image data.

12 Claims, 3 Drawing Sheets

(58) Field of Classification Search
USPC ............................ 378/57, 58, 59, 62, 4, 19
See application file for complete search history.

(56) References Cited

U.S. PATENT DOCUMENTS

2011/0319753 A1* 12/2011 Tout .................. A61K 49/0409
                                                        600/431
2012/0257713 A1* 10/2012 Noel ................... G01N 23/046
                                                        378/19

OTHER PUBLICATIONS

European Search Report from the European Patent Office dated Jul. 19, 2016 for Application No. EP16162596.

* cited by examiner

SYSTEMS AND METHODS FOR RADIOGRAPHIC INSPECTION

BACKGROUND OF THE INVENTION

1. Field of the Invention

The present disclosure relates to non-destructive testing, and more particularly to non-destructive testing and evaluation of components having internal cavities.

2. Description of Related Art

Gas turbine engine components commonly include internal passages and cavities defined within the component. Some internal passages and cavities require dimensional or geometric control for purposes of serving their intended purpose, and therefore can require inspection for purposes of determining whether the internal passages and cavities of a given component conform to part requirements. In order to inspect the component without destroying the component, various non-destructive testing and non-destructive evaluation methods have been developed. For example, eddy-current testing system and methods use electromagnetic induction to detect cracks and other artifacts in a component surface resultant from manufacture, service or repair. Microscopy can also be used to examine external surfaces in detail. Various systems and methods of ultrasonic testing also exist where change in sound waves applied to a component are used to evaluate internal features of components. Penetrating radiation can also be used to inspect the interior of a component, such as with x-rays or neutrons, typically by measuring variation in the attenuation of radiation applied to a component.

Such conventional methods and systems have generally been considered satisfactory for their intended purpose. However, there is still a need in the art for improved systems and methods for inspecting internal features of components. The present disclosure provides a solution for this need.

SUMMARY OF THE INVENTION

An inspection method includes introducing a mixture of expanding foam and a particulate material into a region of interest of an object, fixing the powder within the region of the interest relative to the object, and acquiring image data of the object and particulate mixture using an x-ray source and an x-ray detector. The particulate has a density that is greater than the density of a material forming the object to provide contrast between the region of interest and the object in an image generated using the image data.

In certain embodiments the particulate can include a first material, the object can include a second material, and the expanding foam can include a third material. The first material can have a mass attenuation coefficient that is greater than a mass attenuation coefficient of the second material. The expanding foam can have a mass attenuation coefficient that is less than the mass attenuation coefficient of the second material. For example, the particulate can include tungsten, portions of the object defining the region interest can include aluminum, magnesium, steel, stainless steel, nickel-based alloy, or titanium, and the expanding foam can be a compound formed from isocyanate and polyol resin or polyurethane. The particulate can be infused within the foam, thereby forming an infusion of foam and particulate.

In accordance with certain embodiments, the expanding foam can include a suspension or colloid of particulate disposed within the expanding foam. The expanding foam can have two or more constitute compounds, and the particulate can be introduced into the region of interest intermixed with one or more of the expanding foam constituents. The region of interest can include one or flow passages, such as in a gas turbine engine component like a fuel injector or nozzle assembly. It is contemplated that region of interest can include two or more overlapping flow passages defined within the object.

It is also contemplated that, in accordance with certain embodiments, the method can include removing the particulate from the region of interest. Removing the particulate from the region of interest can include introducing a solvent into the object hollow portion and mobilizing the particulate by dissolving the expanding foam in an expanded state. The method can include generating image data including a point cloud data set. The point cloud data set can be representative of a distribution of the particulate within the region of interest.

A computed tomography method can be applied to the image data to reconstruct an image of the region of interest. The reconstruction can be a three-dimensional reconstruction, based on a contiguous sequence of two-dimensional slices of the region of interest, acquired by exposing the object to x-rays generated by an x-ray source, differently attenuated the respective materials forming the particulate and object, and measured by an x-ray detection arranged on a side of the object opposite the x-ray source. The reconstruction can thereafter be compared to a three-dimensional model of the region of interest.

An inspection system includes an x-ray source, an x-ray detector separated from the x-ray source by an object space, a processor operably associated with the x-ray source and the x-ray detector; and a memory communicative with the processor. The memory can have instructions on the memory that, when read by the processor, cause the processor to execute the method described above.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION OF THE PREFERRED EMBODIMENTS

Figure 1:
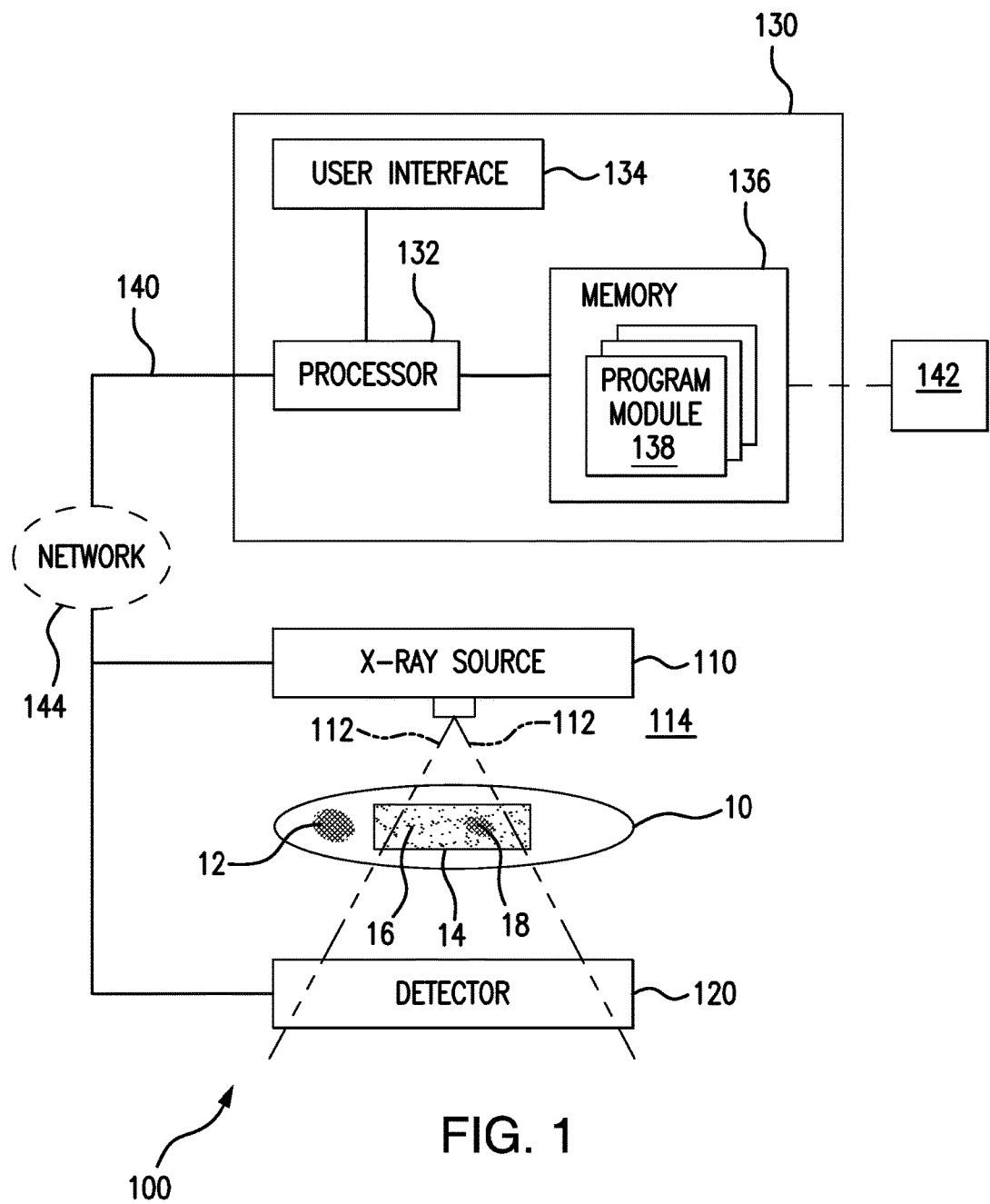
FIG. 1 is a schematic view of an exemplary embodiment of a radiographic inspection system constructed in accordance with the present disclosure, showing an object defining a region of interest disposed between an x-ray source and an x-ray detector.

Reference will now be made to the drawings wherein like reference numerals identify similar structural features or aspects of the subject disclosure. For purposes of explanation and illustration, and not limitation, a partial view of an exemplary embodiment of an inspection system in accordance with the disclosure is shown in FIG. 1 and is designated generally by reference character 100. Other embodiments of radiographic inspection systems and methods in accordance with the disclosure, or aspects thereof, are provided in FIGS. 2-3, as will be described. The systems and methods described herein can be used for inspecting and evaluating regions for interest within objects like gas turbine engine fuel injectors.

With reference to FIG. 1, inspection system 100 is shown. Inspection system 100 includes an x-ray source 110, an x-ray detector 120, and a controller 130 housing a processor 132. Processor 132 is operatively associated with both x-ray source 110 and x-ray detector 120 such that x-ray source 110 emits x-ray radiation 112 toward x-ray detector 120 and through an object space 114 defined between x-ray source 110 and x-ray detector 120. X-ray detector 120 is configured to receive x-ray radiation 112, convert the received 112 into image data, and communicate the image data to processor 132.

An object 10 is disposed between x-ray source 110 and x-ray detector 120. Object 10 defines within its interior a region of interest 14. An expanding foam 18 and particulate 16 are disposed within region of interest 14. Object 10 may be a gas turbine engine component having an internal flow passage or overlapping flow passages, such as a fuel injector.

Particulate 16 includes a first material, object 10 includes a second material 12, and expanding foam 18 includes a third material. The first material forming particulate 16 has a mass attenuation coefficient that is greater than the mass attenuation coefficient of second material 12. Expanding foam 18 has a mass attenuation coefficient that is less than the mass attenuation coefficient of second material 12. Particulate 16 can include, by way of non-limiting example, tungsten powder. Object 10 may include, by way of non-limiting example, aluminum, magnesium, steel, stainless steel, nickel-based alloy, or titanium. Expanding foam 18 may include, by way of non-limiting example, polyurethane or a compound formed from isocyanate and polyol resin.

Figure 2A:
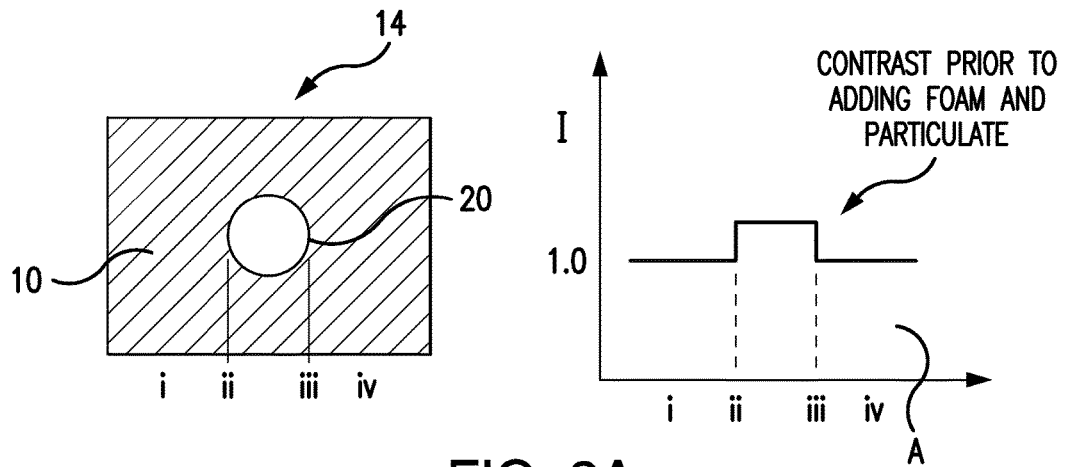
FIG. 2A is a schematic view of the object of FIG. 1, showing attenuation of incident radiation on solid and hollow portions of the object.
Figure 2B:
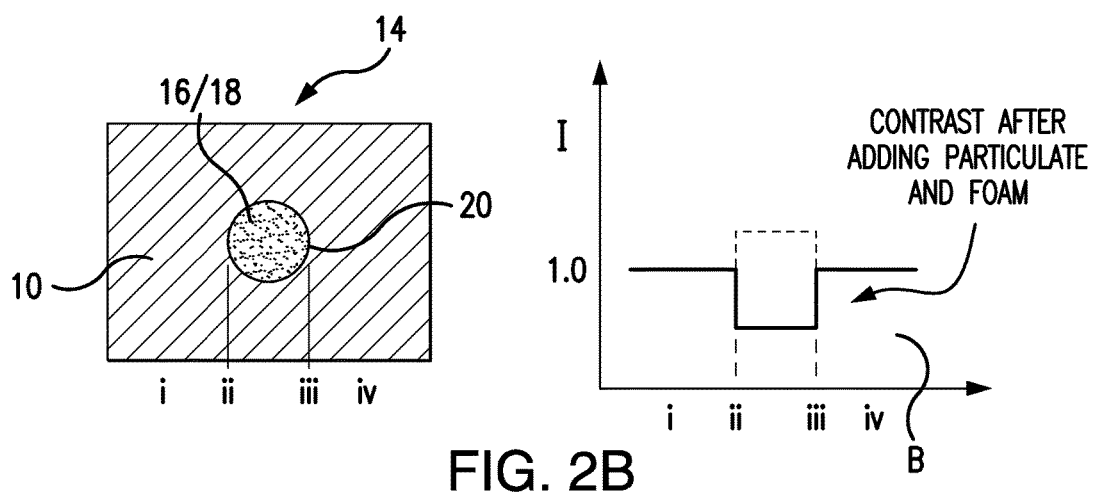
FIG. 2B is a schematic view of the object of FIG. 1 with a hollow interior portion occupied by a particulate and foam mixture, showing increased contrast due to the attenuation of incident radiation attributable to the particulate and foam.
Figure 2C:
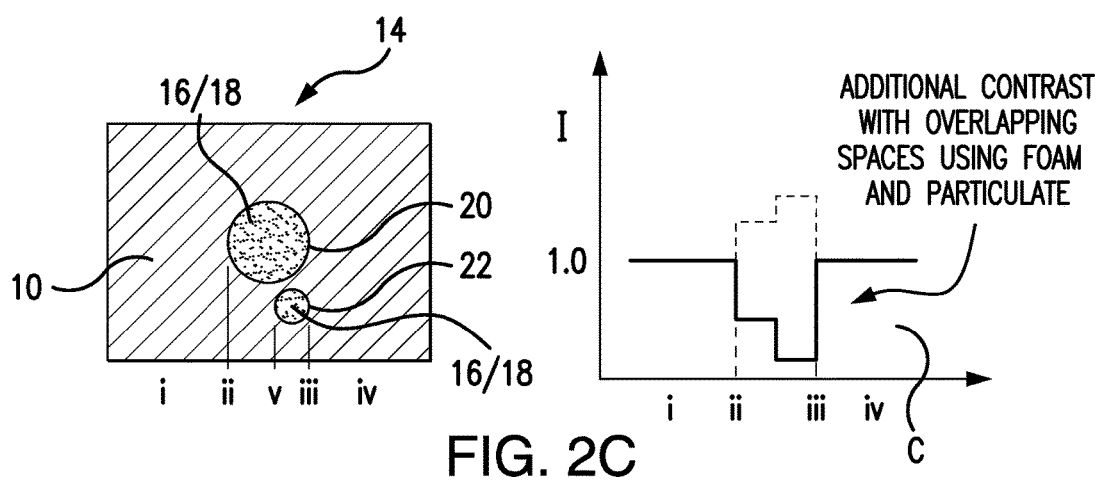
FIG. 2C is a schematic view of an object having overlapping hollow interior portions occupied by a particulate and foam mixture, showing increased contrast in the overlapping hollow interior portions to the particulate and foam disposed therein.

With reference to FIGS. 2A-2C, object 10 and corresponding intensity plots are shown for different interior conditions. With reference to FIG. 2A, object 10 is shown with region of interest 14 having a channel or conduit 20 defined therein. An intensity chart A illustrates the contrast between the solid portions of object 10, e.g. locations (i) and (iv), and a portion housing channel or conduit 20, i.e. between locations (ii) and (iii). Contrast in a radiographic image or reconstruction acquired under this imaging condition is indicated by the range between the y-axis maximum and minimum values on chart A.

With reference to FIG. 2B, object 10 is shown with channel or conduit 20 containing particulate 16 and expanding foam 18. Due to the attenuation properties of particulate 16, the portion of region of interest 14 housing channel or conduit 20, i.e. between locations (ii) and (iii), contrast in a radiographic image or reconstruction acquired under this imaging condition, as indicated by the range between the y-axis maximum and minimum values on chart B. In the illustrated exemplary embodiment, the contrast in the imaging condition illustrated in FIG. 2B is about twice that illustrated in FIG. 2A (and reproduced in FIG. 2B in dashed outline). As will be appreciated, the contrast range can be increased or decreased by increasing the ratio of particulate to foam introduced into channel or conduit 20.

With reference to FIG. 2C, object 10 is shown with a second channel or conduit 22 overlapping first channel or conduit 20. Both first channel or conduit 20 and overlapping second channel or conduit 22 contain particulate 16 and expanding foam 18. As above, due to the attenuation properties of particulate 16, the portion of region of interest 14 housing both first channel or conduit 20 and second channel or conduit 22, i.e. between locations (v) and (iii), appears with greater contrast than that illustrated in Chart B (shown in FIG. 2B). This additional contrast makes it possible to acquire imaging data where overlapping hollow portions of an object are distinguishable based on increased contrast relative non-overlapped hollow portions of the object.

Figure 3:
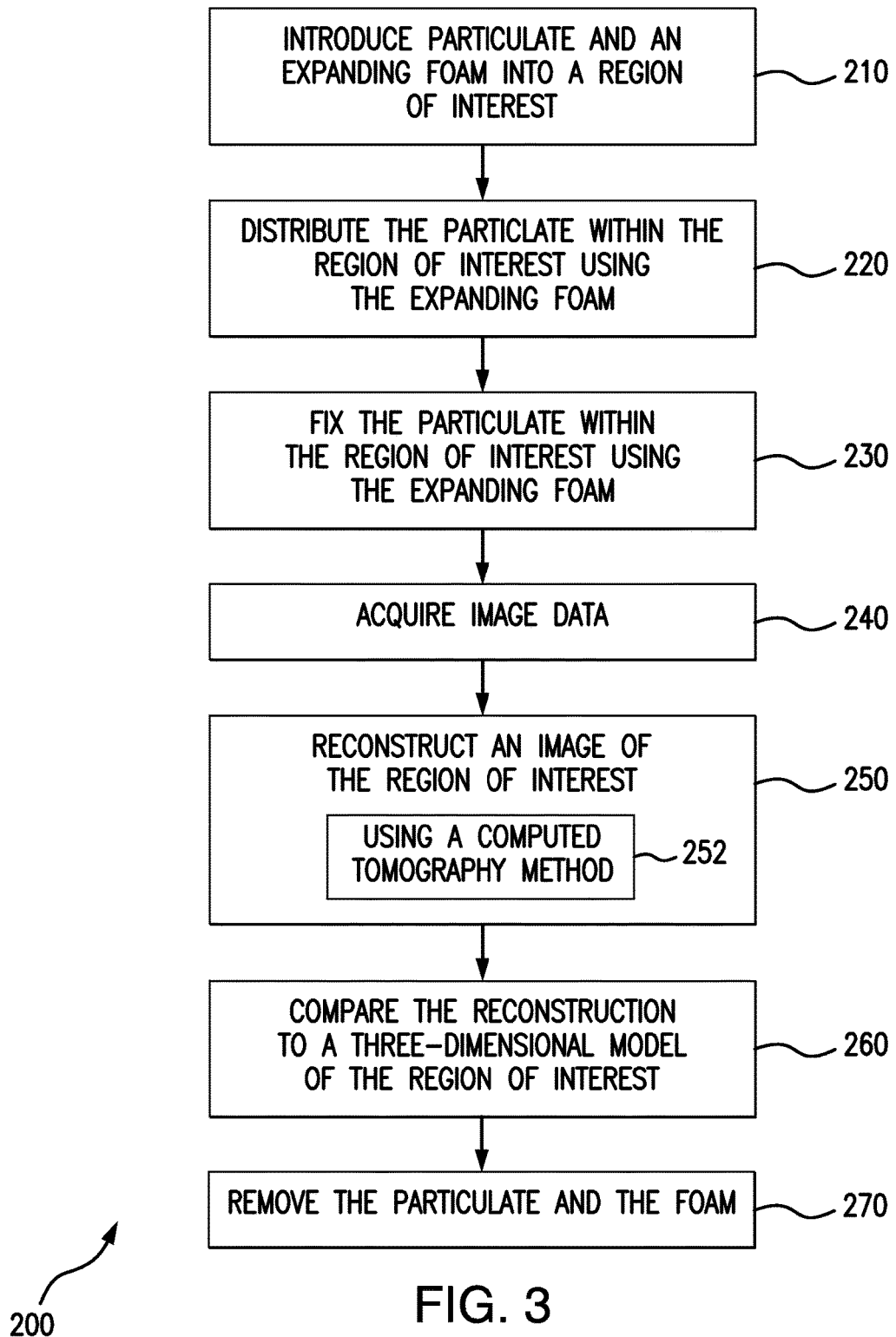
FIG. 3 is a method for inspecting a region of interest by imaging the region of interest after introducing a mixture of particulate and foam into a hollow portion of the region of interest.

With reference to FIG. 3, an inspection method 200 is shown. Inspection method 200 includes introducing a mixture of expanding foam and a particulate material into a region of interest of an object, as shown with box 210. The expanding foam, e.g. expanding foam 18, drives the particulate, e.g. particulate 16, into cavities and/or conduits defined within the region of interest of the object. This distributes the particulate within the region of interest using the expanding foam as shown with box 220, increasing contrast between the region of interest and the object defining (i.e., bounding) the region of interest.

As the foam disperses within the region of interest, the expanded foam fixes the powder within the region of the interest relative to the object, as shown with box 230. The expanding foam may include open-cell expanding foam or closed-cell expanding foam. Open-cell foam allows for distributing the particulate into confined features as the open cells leave egress channels within the foam for conveying displaced gas (e.g., air) to the environment external to object 10.

The expanding foam may include a suspension or colloid of particulate disposed within the expanding foam. As will be appreciated, in embodiments using a suspension of particulate within expanding foam, gravity can be used to assist distribution of the particulate within the foam prior to the foam curing. In embodiments using a colloid mixture of particulate and expanding foam, the distribution of the particulate can be more uniform throughout the foam in its cured state.

Inspection method 200 further includes acquiring image data of the object and particulate mixture using an x-ray source and an x-ray detector, e.g. x-ray source 110 and x-ray detector 120, as shown with box 240. It is to be understood and appreciated that the greater density of the particulate in relation to the forming the object provides greater contrast between the region of interest and the object in an image generated using the image data. This can make relatively small features within the region of interest more readily discernable within the image data.

Once the image data is obtained, a reconstruction is generated of the region of interest, as shown with box 250. The reconstruction can be generated using a computed tomography method, a shown with box 252. Using point-cloud data, points between points of high attenuation can be assigned the average intensity of adjacent point of high attenuation to make space occupied by the expanding foam during the image data collection operation appear similar to space occupied by particles during imaging.

Reconstructing the image may include reconstructing a three-dimensional reconstruction based on a contiguous sequence of two-dimensional slice image data of the region of interest, acquired by exposing the object to x-rays generated by an x-ray source, differently attenuated the respective materials forming the particulate and object, and measured by an x-ray detection arranged on a side of the object opposite the x-ray source. The reconstruction can thereafter be compared to a three-dimensional model of the region of interest, as shown with box 260.

Inspection method 200 also includes removing the particulate and expanding foam from the region of interest, as shown with box 270. Removing the particulate and expanding foam may include introducing a solvent into the region of interest, dissolving the expanding foam, and mobilizing the particulate. Channel defined within open-cell expanding foam would facilitate dissolving the expanding foam due to the access provided by channels therein to the solvent to expanding foam disposed within region of interest not otherwise readily accessible.

Returning to FIG. 1, controller 130 includes a user interface 134 and a memory 136 communicative with processor 132. User interface 134 preferably includes an input device, such as a keyboard, a touch screen or a speech recognition subsystem, which enables a user to communicate information and command selections to processor 132. User interface 134 may also include an output device such as a display, e.g., a multi-function display. User interface 134 may also further include an input device such as a mouse, track-ball, or joystick, which allows a user to manipulate the display for communicating additional information and command selections to processor 132.

Processor 132 is preferably an electronic device configured of logic circuitry that responds to and executes instructions. Memory 136 is preferably a computer-readable medium encoded with a computer program. In this regard, memory 136 stores data and instructions readable and executable by processor 132 for controlling the operation of processor 132. Memory 136 may be implemented in a random access memory (RAM), a hard drive, a read only memory (ROM), or a combination thereof.

Program module 138 contains instructions that cause processor 132 to execute the methods described herein. For example, under control of program module 138, processor 132 issues instructions x-ray source 110 and x-ray detector 120 in cooperation with one another such that x-ray detector 120 generates image data which it provides to controller 130 over a communications bus 140. Program module 138 can also include geometric information relating to object 10, such three-dimensional model data relating to object 10 and region of interest 14 for purposes of comparing to a reconstruction region of interest 14 as imaged with expanding foam 18 and particulate 16 disposed therein. It is to be appreciated that the term "module" is used herein to denote a functional operation that may be embodied either as a stand-alone component or as an integrated configuration of a plurality of sub-ordinate components. Thus, program module 138 may be implemented as a single module or as a plurality of modules that operate in cooperation with one another. Moreover, although program module 138 is described herein as being installed in memory 136, and therefore being implemented in software, it could be implemented in any of hardware (e.g., electronic circuitry), firmware, software, or a combination thereof.

Processor 132 outputs, to user interface 134, a result of an execution of the methods described herein. Alternatively, processor 132 could direct the output to a remote device (not shown), via a network connected to communications bus 140. It is also to be appreciated that while program module 138 is indicated as already loaded into memory 136, it may be configured on a storage medium 142 (shown in dashed outline) for subsequent loading into memory 136. Storage medium 142 is also a computer-readable medium encoded with a computer program, and can be any conventional storage medium that stores program module 138 thereon in tangible form. Examples of storage medium 142 include a floppy disk, a compact disk, a magnetic tape, a read only memory, an optical storage media, universal serial bus (USB) flash drive, a solid-state storage (SSD), a compact flash card, or a digital versatile disc. Alternatively, storage medium 142 can be a random access memory, or other type of electronic storage, located on a remote storage system and may be optionally coupled to controller 130 via a network 144.

It is further to be appreciated that although the systems and methods described herein can be implemented in software, they could be implemented in any of hardware (e.g., electronic circuitry), firmware, software, or a combination thereof.

Radiographic (x-ray) inspection of some kinds of gas turbine engine components can be difficult. In particular, components having flow passages that overlap or are relatively small can be challenging to image. It can also be difficult to distinguish fine features using conventional radiographic inspection, digital radiography, or computed tomography techniques. This is true for basic casting materials such aluminum and magnesium. Materials with relatively high densities, such as nickel-based alloys in relation to aluminum, can present further challenging to imaging cavities and passages defined within the component.

Introducing a suspension or colloid of high-density particles such as tungsten powder within an expanding foam can make such internal features more readily discernable and easier to inspect using radiographic inspection techniques. This is because the high-density particles can be more readily visible relative to less dense materials when viewing a component during radiographic inspection. Since it is generally considered too difficult to introduce powder stock into confined spaces or convoluted flow passages within a component interior, introducing the particulate into the component suspended within an expanding foam provides a mechanism for driving and distributing the particles within the interior of the region of interest, particularly into convoluted passages. Application of three-dimensional computed tomography techniques can be used to create the equivalent of a point cloud data set that can be compared to a three-dimensional model of the component for purposes of discerning dimensional attributes of an as-built component or identifying manufacturing artifacts within the imaged component.

Once the image data has been acquired, the expanding foam can be dissolved such that the expanding foam and particles are mobilized and removed from the component. As will be appreciated, suspending the particles within the expanding foam can reduce the amount of particulate material necessary to acquire sufficient image data to image the interior of the component.

The methods and systems of the present disclosure, as described above and shown in the drawings, provide for systems and methods of radiographic inspection with superior properties including the ability to image internal cavities within relatively dense components. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. An inspection method, comprising:
introducing a mixture of expanding foam and a particulate into a region of interest of an object;
fixing the particulate relative to the object in the region of interest; and
acquiring image data including the object and particulate using x-ray radiation, wherein a density of the particulate is greater than that of the object to provide contrast between the object and the region of interest in the image data, wherein the object is a fuel injector for a gas turbine engine, wherein the particulate includes a first material and the object includes a second material, the first material having a mass attenuation coefficient that is greater than a mass attenuation coefficient of the second material and wherein the expanding foam includes a third material having a mass attenuation coefficient that is smaller than the mass attenuation coefficient of the second material.

2. The inspection method as recited in claim 1, wherein the particulate includes tungsten and the object includes a material that is less dense than tungsten.

3. The inspection method as recited in claim 1, wherein the object includes at least one of aluminum, magnesium, steel, stainless steel, nickel-based alloy, and titanium.

4. The inspection method as recited in claim 1, wherein the mixture of expanding foam and particulate is a suspension.

5. The inspection method as recited in claim 1, wherein the expanding foam includes an open-cell foam.

6. The inspection method as recited in claim 1, wherein the region of interest includes at least one flow passage.

7. The inspection method as recited in claim 1, wherein the region of interest includes first and second overlapping flow passages.

8. The inspection method as recited in claim 1, wherein the object is fuel injector for a gas turbine engine.

9. The inspection method as recited in claim 1, further including removing the particulate from the object hollow portion by introducing a solvent into the region of interest and dissolving the expanding foam using the solvent.

10. The inspection method as recited in claim 1, wherein the image data includes a point cloud data set representative of a distribution of particulate within the region of interest.

11. The inspection method as recited 10, wherein generating the image data set includes exposing both the expanding foam and the particulate to x-ray radiation, and further including:
reconstructing an image of the region of interest using a computed tomography reconstruction method and the point cloud data set; and
comparing the reconstructed image to a three-dimensional model of the object.

12. An inspection system, comprising:
an x-ray source;
an x-ray detector separated from the x-ray source by an object space;
a processor operably associated with the x-ray source and the x-ray detector; and
a memory communicative with the process and having instructions recorded thereon that, when read by the processor, cause the processor to:
acquire image data using x-ray radiation of a region of interest disposed within the object space, wherein the region of interest includes a mixture of expanding foam and a particulate fixed within the object space and within is a fuel injector for a gas turbine engine, wherein the particulate includes a first material and the object includes a second material, the first material having a mass attenuation coefficient that is greater than a mass attenuation coefficient of the second material and wherein the expanding foam includes a third material having a mass attenuation coefficient that is smaller than the mass attenuation coefficient of the second material;
reconstruct the region of interest using a computed tomography reconstruction method; and
compare the reconstruction to a three-dimensional model of the object.

* * * * *